(12) United States Patent
Duttaroy

(10) Patent No.: US 9,987,317 B2
(45) Date of Patent: Jun. 5, 2018

(54) CARDIO-PROTECTIVE AGENTS FROM KIWIFRUITS

(75) Inventor: Asim Kanti Duttaroy, Oslo (NO)

(73) Assignee: UNIVERSITY OF OSLO, Oslo (NO)

( * ) Notice: Subject to any disclaimer, the term of this patent is extended or adjusted under 35 U.S.C. 154(b) by 66 days.

(21) Appl. No.: 13/991,497

(22) PCT Filed: Dec. 6, 2011

(86) PCT No.: PCT/US2011/063454
§ 371 (c)(1),
(2), (4) Date: Jul. 2, 2013

(87) PCT Pub. No.: WO2012/078587
PCT Pub. Date: Jun. 14, 2012

(65) Prior Publication Data
US 2014/0314889 A1  Oct. 23, 2014

Related U.S. Application Data

(60) Provisional application No. 61/490,246, filed on May 26, 2011, provisional application No. 61/420,499, filed on Dec. 7, 2010.

(51) Int. Cl.
| A61K 36/185 | (2006.01) |
| A23L 2/02 | (2006.01) |
| A23L 33/105 | (2016.01) |

(52) U.S. Cl.
CPC .............. *A61K 36/185* (2013.01); *A23L 2/02* (2013.01); *A23L 33/105* (2016.08); *A61K 2236/39* (2013.01)

(58) Field of Classification Search
CPC .... A61K 36/185; A23L 1/3002; A23L 33/105
See application file for complete search history.

(56) References Cited

U.S. PATENT DOCUMENTS

| 4,795,742 | A  * | 1/1989 | Liu ................................. 514/26 |
| 6,617,337 | B1 * | 9/2003 | Wilcox .......................... 514/315 |
| 7,851,458 | B2 * | 12/2010 | Stone .............................. 514/62 |
| 2004/0037909 | A1 | 2/2004 | Kim et al. |
| 2007/0259059 | A1 | 11/2007 | Eidenberger |
| 2008/0175888 | A1 | 7/2008 | Lindemann |
| 2010/0111927 | A1 | 5/2010 | Kim |
| 2010/0143319 | A1 | 6/2010 | Weir |
| 2013/0122128 | A1* | 5/2013 | Kim et al. ..................... 424/777 |

FOREIGN PATENT DOCUMENTS

| EP | 1186297 A2 | 3/2002 |
| JP | 3009441 | 4/1992 |
| JP | 6-135830 | 5/1994 |
| JP | 7-324037 | 12/1995 |
| JP | 2002-08357 | 3/2002 |
| JP | 2006-503566 | 2/2006 |
| JP | 2007-217396 | 8/2007 |
| JP | 2008259486 | 10/2008 |
| WO | 2004/037017 | 5/2004 |
| WO | 2005/096840 | 10/2005 |
| WO | 2006/016728 | 2/2006 |
| WO | 2012/078587 | 6/2012 |

OTHER PUBLICATIONS

Bordia et al. The Effect of Vitamin C on Blood Lipids, Fibrinolytic Activity and Platelet Adhesiveness in Patients With Coronary Artery Disease. vol. 35, Issue 2, pp. 181-187 Feb. 1980.*
H.B. MacPhillamy: Drugs From Plants; Plant Science Bulletin, Botanical Society of America, vol. 9, No. 2, Apr. 1963.*
Minor Fruits; Hardy Kiwifruit Actinidia Arguta; Online, URL< http://www.fruit.cornell.edu/mfruit/kiwifruit.html> 3 pages, accessed Feb. 17, 2015.*
NaturalHub.com: Natural Food Guid-Fruit Vitamin C Content of Actinidia Species (Kiwifruit) & Cultivars: Online, URL<https://web.archive.org/web/20060203081920/http://www.naturalhub.com/natural_food_guide_fruit_vitamin_c_actinidia.htm> 5 pages, Feb. 3, 2006 (archived by www.archive.org).*
Phillipson, J. New Drugs From Nature—IT Could Be Yew; Phytotherapy Research 13 (1999) pp. 2-8.*
Raskin et al. Can an Apple a Day Keep the Doctor Away? Current Pharmaceutical Design, 2004, 10, 3419-3429.*
Revilla et al. Comparison of Several Procedures Used for the Extraction of Anthocynains From Red Grapes; J. Agric. Food Chem. 1998, 46, pp. 4592-4597.*
Schowalter, TD: Insect Ecology; An Ecosystem Approach; Third Ed., Academic Press, London, UK, 2011, pp. 71-73.*
Fiorentino, Antonio, "Identification and Assessment of Antioxidant Capacity of Phytochemicals from Kiwi Fruits," J. Agric. Food Chem (2009), 57, 4148-4155.
Jantan, Ibrahim, et al., "Antiplatelet aggregation activity of compounds isolated from Guttiferae species in human whole blood," Pharmaceutical Biology (2009) 47(11): 1090-1095.
CN Office Action dated Jul. 15, 2014 from related CN Patent Application No. 201180065095.X and English Translation).
Shaomei, Huang, "Process for preparing kiwifruits juice", Journal of Science and Technology of Food Industry, p. 44, Dec. 31, 1990 (English translation not provided).
Asgeir Brevik et al., "Supplementation of a western diet with golden kiwifruits (*Actindia chinensis* var.'Hort 16A') effects on biomarkers of oxidation damage and antioxidant protection", Nutrition Journal, vol. 10, No. 1, May 18, 2011, p. 54.
Chang Wen-Hsin et al., "Effects of kiwifruit consumption on serum lipid profiles and antioxidative status in hyperlipidemic subjects," International Journal of Food Sciences and Nutrition, Dec. 2009, vol. 60, No. 8, Dec. 2009, pp. 709-716.

(Continued)

*Primary Examiner* — Christopher R Tate
*Assistant Examiner* — Aaron J Kosar
(74) *Attorney, Agent, or Firm* — Casimir Jones S.C.; J. Mitchell Jones

(57) ABSTRACT

The invention relates to cardio-protective agents. In particular, the present invention relates to cardio-protective extracts and fractions thereof prepared from kiwi fruit.

1 Claim, 7 Drawing Sheets

(56) References Cited

OTHER PUBLICATIONS

Database WPI Week 201036 Thomson Scientific, London, GB; AN 2010-F55348, XP002668785, with English abstract of CN 101 704 899 A.
Database WPI Week 201053 Thomson Scientific, London, GB; AN 2010-K18284, XP002668786, with English abstract of CN 101 756 320 A.
Duttaroy, Asim K., et al., "Effects of kiwi fruit consumption on platelet aggregation and plasma lipids in healthy human volunteers", Platelets, Taylor and Francis Group, Edinburgh, vol. 15, No. 5, Aug. 2004, pp. 287-292.
International Search Report and Written Opinion dated Feb. 20, 2012, PCT/US2011/063454.
International Search Report and Written Opinion, PCT/US2013/026826, dated Jul. 11, 2013.
Jung Kyung-Ah, et al., "Cardiovascular protective properties of kiwifruit extracts in vitro," Biological & Pharmaceutical Bulletin (of Japan), Pharmaceutical Society of Japan, Tokyo, JP, vol. 28, No. 9, Sep. 1, 2005, pp. 1782-1785.
Karlsen, A., et al., "Kiwifruit decreases blood pressure and whole-blood platelet aggregation in male smokers," Journal of Human Hyptertension 2013, Nature Publishing Group GBR, vol. 27, No. 2, Jan. 19, 2012, pp. 126-130.
Nagai Takeshi, et al., "Functional properties of water extracts from fully ripened silver vine (*Actinidia polygama*(Sieb. Et Zucc.) Planch. Ex Maxim.) berries," Journal of Food Agriculture & Environment, vol. 6, No. 3-4, Jul. 2008, pp. 11-14.
Sun-Waterhouse Dongxiao et al., "Kiwifruit-based polyphenols and related antioxidants for functional foods: kiwifruit extract-enhanced gluten-free bread," International Journal of Food Sciences and Nutrition 2009, vol. 60, Supp 7, 2009, pp. 251-264.
Daigo Abe, et al., "A fraction of unripe kiwi fruit extract regulates adipocyte differentiation and function in 3T3-L1 cells", Biofactors, vol. 36, No. 1, Jan./Feb. 2010, pp. 52-59.
Dutta-Roy, Asim K., "Dietary components and human platelet activity", Platelets, 2002, 13(2): 67-75.
Dutta-Roy, A.K., et al., "Effects of tomato extract on human platelet aggregation in vitro", Platelets, 2001, 12(4): 218-27.
Nishiyama I., "Fruits of the Actinidia Genus", Advances in Food and Nutrition Research, 2007, vol. 52, pp. 293-324.
Nishiyama "Compositional Changes in Fruit of Kiwifruit during Postharvest Ripening" 2006, Komazawa Women's Junior College Research Journal, vol. 39, pp. 55-60.
Cano "HPLC Separation of Chlorophyll and Carotenoid Pigments of Four Kiwi Fruit Cultivars" (1991) J. Agric. Food Chem. 39, pp. 1786-1791.
Kim et al. "Effects of Orally Administered Actinidia arguta (Hardy Kiwi) Fruit Extract on 2-Chloro-1,3,5-Trinitrobenzene-Induced Atopic Dermatitis-Like Skin Lesions in NC/Nga Mice" (2009) J. Med Food 12(5): 1004-1015.
Latocha et al. "Antioxidant activity and chemical difference in fruit of difference *Actinidia* sp." (2010) Int. J. Food Sci. and Nutr. 61(4): 381-394.
Shehata et al. "Effects of Bioactive Component of Kiwi Fruit and Avacado (Fruit and Seed) on Hypercholesterolemic Rats" (2013) World J Dairy & Food Sci. 8(1): 82-93.
Wang et al. "Isolation of an antifungal thaumatin-like protein from kiwi fruits" (2002) Phytochemistry 61: 1-6.
Cheplick S. et al. "Clonal Variation in Raspberry Fruit Phenolics and Relevance for Diabetes and Hypertension Management", Journal of Food Biochemistry, 2007, 31(5), pp. 656-679.
Dawes and Keene "Phenolic Composition of Kiwifruit Juice" J. Agric. Food Chem. 1999, 47, 2398-2403.
Bursal and Guicin Polyphenol contents and in vitro antioxidant activities of lyophilised aqueous extract of kiwifruit (*Actinidia deliciosa*), Food Res Int, 2011, vol. 44, No. 5, p. 1482-1489.
Kaya et al. "Effect of difference drying conditions on the vitamin C (ascorbic acid) content of Hayward kiwifruits (*Actinidia deliciosa* Planch)" Food and Bioproducts Processing, 88 (2010), pp. 165-173.
Namiki et al. "Platelet Aggregation Inhibitory Activity of Tea Extracts" Nippon Shokuhin Kogyo Gakkaishi, 1991, vol. 38, No. 3, pp. 189-195, English summary provided.

* cited by examiner

CARDIO-PROTECTIVE AGENTS FROM KIWIFRUITS

FIELD OF THE INVENTION

The invention relates to cardio-protective agents. In particular, the present invention relates to cardio-protective extracts and fractions thereof prepared from kiwi fruit.

BACKGROUND OF THE INVENTION

It is known that a high consumption of fruits and vegetables is an important preventive measure by which risk of cardiovascular diseases and certain nutritionally linked cancers including stomach, colon, breast, and prostate cancer can be decreased. One factor involved in the initiation and development of both cardiovascular diseases and cancers is the occurrence of abnormal oxidative stress processes leading to the generation of hydroxy and peroxy free radicals or compounds. In part, the beneficial effect of eating fruits and vegetables is explained by the antioxidants known to account for the inhibition include vitamin C, vitamin E and carotenoids such as alpha and beta carotenoids, lycopene lutein, etc. However, many emerging data also indicates a role for non-antioxidant properties of some compounds in fruits in different diseases.

Considerable effort has been expended in identifying bioactive compounds derived from fruits and vegetables may have a role in the prevention of some diseases. Fruits and vegetables have been thought to be beneficial in cardiovascular disease. The beneficial effects of fruits and vegetables may be explained by antioxidants and bioactive non-antioxidant components contained therein. These compounds may function individually or in concert to protect lipoproteins and vascular cells from oxidation, or by other mechanisms (non-antioxidant pathways) such as reducing plasma lipid levels (LDL cholesterol, triglycerides), and platelet aggregation response (1,2).

Additional preparations from fruits and vegetables that provide cardio-protective and other beneficial properties are needed.

SUMMARY OF THE INVENTION

The invention relates to cardio-protective agents in fruits. In particular, the present invention relates to cardio-protective extracts and fractions thereof prepared from kiwi fruit.

In some embodiments, the present invention provides a composition comprising, in whole or in part, a fruit extract from a fruit of the family *Actinidia*, said extract characterized as being stable and retaining biological activity during storage. In other embodiments, the present invention provides a fruit extract or fraction from a fruit of the family *Actinidia*, said extract stabilized to retain biological activity during storage. In some embodiments, the fruit extract or fraction is stabilized by heat treatment. In some embodiments, the heat treatment is sufficient to stabilize the biological activity of the extract. In some embodiments, the heat treatment comprises heating to about 70 to 120 degrees Celsius, and more preferably to about 80 to 100 degrees Celsius. In some embodiments, the fruit extract or fraction is stabilized by removal of enzymes in the fraction, for example by ultrafiltration. In some embodiments, the biological activity is inhibition of platelet aggregation in an in vitro platelet aggregation assay. In some embodiments, the extract or fraction has more than 4% inhibitory activity in an in vitro platelet aggregation assay after kept at 4 degrees Celsius for 24 days normalized to day 0. In some embodiments, the extract or fraction may be further characterized as retaining at least 80% of biological activity of said biologically active molecules when stored for 4 days at 4 degrees Celsius as compared to a fresh extract fraction, wherein said biological activity is inhibition of platelet aggregation in an in vitro platelet aggregation assay. In some embodiments, the extract or fraction may be further characterized as retaining at least 80% of biological activity of said biologically active molecules when stored for at least 18 days at 4 degrees Celsius as compared to a fresh extract fraction, wherein said biological activity is inhibition of platelet aggregation in an in vitro platelet aggregation assay. In some embodiments, the extract or fraction may be further characterized as retaining at least 80% of biological activity of said biologically active molecules when stored for at least 24 days at 4 degrees Celsius as compared to a fresh extract fraction, wherein said biological activity is inhibition of platelet aggregation in an in vitro platelet aggregation assay. In some embodiments, the biological activity is inhibition of angiotensin-converting enzyme.

In some embodiments, the extract or fraction is delipidated. In some embodiments, the extract or fraction comprises biologically active molecules with a molecular weight of less than 3000 daltons. In some embodiments, the extract or fraction comprises biologically active molecules with a molecular weight of less than 1000 daltons. In some embodiments, the fruit extract or fraction exhibits major peaks at approximately 1.30 and 1.81 minutes on a UV spectrum scan of liquid chromatography of said extract on a Zorbax 1.8 µM particle rapid resolution C18 column (4.6 mm×50 mm, 1.8 µm) with a 100% mobile phase (A) water-formic acid (100:0.1, v/v/v) to 100% B acetonitrile-formic acid (100:0.1, v/v/v) during 35 minutes. In some embodiments, the extract or fraction exhibits major UV spectrum peaks as observed in FIG. 6. In some embodiments, the fruit extract exhibits major peaks at approximately 1.61, 30.18, and 30.87 in a mass spectometry 100-1000 Mw in negative mode scan of liquid chromatography of said extract on a Zorbax 1.8 µM particle rapid resolution C18 column (4.6 mm×50 mm, 1.8 µm) with a 100% mobile phase (A) water-formic acid (100:0.1, v/v/v) to 100% B acetonitrile-formic acid (100:0.1, v/v/v) during 35 minutes. In some embodiments, the extract or fraction exhibits major total ion current chromatogram peaks as observed in FIG. 7.

In some embodiments, the present invention provides a syrup or solution comprising an extract or fraction as described above. In some embodiments, the present invention provides a powder comprising the extract or fraction as described above. In some embodiments, the present invention provides an oral delivery vehicle comprising the extract or fraction, or syrup, solution or powder thereof as described above. In some embodiments, the present invention provides a functional food or foodstuff comprising the composition, syrup, solution or powder as described above. In some embodiments, the functional food or foodstuff is selected from the group consisting of beverages, baked goods, puddings, dairy products, confections, snack foods, frozen confections or novelties, prepared frozen meals, candy, snack products, soups, spreads, sauces, salad dressings, prepared meat products, cheese, and yogurt. In some embodiments, the present invention provides a nutritional supplement comprising the composition, syrup, solution or powder as described above. In some embodiments, the nutritional supplement is selected from the group consisting of soft gel capsules, hard shell capsules, chewable capsules, health bars, and supplement powders.

In some embodiments, the present invention provides methods of preventing or treating a disease state initiated or characterized by platelet activation and/or aggregation, improving or maintaining heart health, improving or maintaining cardiovascular health, improving or maintaining circulatory health, or improving or maintaining blood flow in a subject comprising administering to said subject a fruit extract or fraction, or syrup, powder, oral delivery vehicle or nutritional product as described above. In some embodiments, the administering inhibits platelet aggregation. In some embodiments, the administering results in anti-thrombotic activity. In some embodiments, the administering results in blood thinning. In some embodiments, the administering results in reduced blood pressure.

In some embodiments, the present invention provides for the use of the extract or fraction, or syrup, powder, oral delivery vehicle or nutritional product as described above for preventing or treating a disease state initiated or characterized by platelet activation and/or aggregation, improving or maintaining heart health, improving or maintaining cardiovascular health, improving or maintaining circulatory health, or improving or maintaining blood flow in a subject, or improving or maintaining blood pressure in a subject. In some embodiments, the disease state initiated or characterized by platelet activation and/or aggregation is selected from the group consisting of thrombosis, arteriosclerosis and and/or plaque formation.

In some embodiments, the present invention provides processes for producing a stable and biologically active *Actinidia* extract comprising producing an *Actinidia* extract and heating the *Actinidia* extract under conditions such that the extract retains biological activity during storage. In some embodiments, the heating step comprises heating said fraction to about 70 to about 100 degrees Celsius for greater than about five minutes. In some embodiments, the *Actinidia* extract is produced by sedimenting an *Actinidia* juice or homogenate either before or after heating to provide a sediment fraction and a supernatant fraction, and retaining said supernatant fraction to provide said biologically active *Actinidia* extract. In some embodiments, the sedimentation step comprises centrifugation at at least 3000 g. In some embodiments, the extract is additionally processed by ultrafiltration either before or after heating. In some embodiments, the ultrafiltration has a cut-off of between 1000-3000 Daltons.

In some embodiments, the present invention provides a stable and biologically active *Actinidia* extract produced by the foregoing processes. In some embodiments, the stable and biologically active *Actinidia* extract of Claim 35, wherein said extract exhibits major peaks at approximately 1.30 and 1.81 minutes in a UV spectrum scan of liquid chromatography of said extract on a Zorbax 1.8 µM particle rapid resolution C18 column (4.6 mm×50 mm, 1.8 µm) with a 100% mobile phase (A) water-formic acid (100:0.1, v/v/v) to 100% B acetonitrile-formic acid (100:0.1, v/v/v) during 35 minutes and major peaks at approximately 1.61, 30.18, and 30.87 in a mass spectometry 100-1000 Mw in negative mode scan of liquid chromatography of said extract on a Zorbax 1.8 µM particle rapid resolution C18 column (4.6 mm×50 mm, 1.8 µm) with a 100% mobile phase (A) water-formic acid (100:0.1, v/v/v) to 100% B acetonitrile-formic acid (100:0.1, v/v/v) during 35 minutes, and wherein said extract inhibits platelet aggregation in an in vitro platelet aggregation assay. In some embodiments, the stable and biologically active *Actinidia* extract described above is characterized in retaining more than 4% of biological activity of said biologically active molecules when stored for at least 24 days at 4 degrees Celsius as compared to a fresh extract fraction, wherein said biological activity is inhibition of platelet aggregation in an in vitro platelet aggregation assay.

In other embodiments, the present invention provides a fruit extract fraction, wherein the fraction comprises biological molecules with a molecular weight of less than 3000, 2000 or 1000 daltons. In some embodiments, the extract is delipidated. In some embodiments, the fruit is a fruit of the family *Actinidia*. In some embodiments, the extract is stabilized by heat treatment. In some embodiments, the heat treatment comprises heating to about 70 to 100 degrees Celsius. In some embodiments, the fruit extract exhibits major peaks at approximately 1.30 and 1.81 minutes on a UV spectrum scan of liquid chromatography of said extract on a Zorbax 1.8 µM particle rapid resolution C18 column (4.6 mm×50 mm, 1.8 µm) with a 100% mobile phase (A) water-formic acid (100:0.1, v/v/v) to 100% B acetonitrile-formic acid (100:0.1, v/v/v) during 35 minutes. In some embodiments, the extract exhibits major UV spectrum peaks as observed in FIG. 6. In some embodiments, the fruit extract exhibits major peaks at approximately 1.61, 30.18, and 30.87 in a mass spectometry 100-1000 Mw in negative mode scan of liquid chromatography of said extract on a Zorbax 1.8 µM particle rapid resolution C18 column (4.6 mm×50 mm, 1.8 µm) with a 100% mobile phase (A) water-formic acid (100:0.1, v/v/v) to 100% B acetonitrile-formic acid (100:0.1, v/v/v) during 35 minutes. In some embodiments, the extract exhibits major total ion current chromatogram peaks as observed in FIG. 7.

In some embodiments, the present invention provides an *Actinidia* extract fraction comprising biologically active molecules with a molecular weight of less than 3000, 2000, or 1000 daltons, wherein said extract exhibits major peaks at approximately 1.30 and 1.81 minutes in a UV spectrum scan of liquid chromatography of said extract on a Zorbax 1.8 µM particle rapid resolution C18 column (4.6 mm×50 mm, 1.8 µm) with a 100% mobile phase (A) water-formic acid (100:0.1, v/v/v) to 100% B acetonitrile-formic acid (100:0.1, v/v/v) during 35 minutes and major peaks at approximately 1.61, 30.18, and 30.87 in a mass spectometry 100-1000 Mw in negative mode scan of liquid chromatography of said extract on a Zorbax 1.8 µM particle rapid resolution C18 column (4.6 mm×50 mm, 1.8 µm) with a 100% mobile phase (A) water-formic acid (100:0.1, v/v/v) to 100% B acetonitrile-formic acid (100:0.1, v/v/v) during 35 minutes, and wherein said extract inhibits platelet aggregation in an in vitro platelet aggregation assay.

In some embodiments, the present invention provides processes for producing a stable and biologically active *Actinidia* extract comprising: fractionating juice from an *Actinidia* fruit to produce and extract fraction and heating said extract fraction to about 70 to about 100 degrees Celsius. In some embodiments, the fractionating comprises size fractionation. In some embodiments, the heating comprises heating said fraction to said about 70 to about 100 degrees Celsius for greater than about five minutes. In some embodiments, the present invention provides a stable and biologically active *Actinidia* extract produced by the foregoing method. In some embodiments, the stable and biologically active *Actinidia* extract exhibits major peaks at approximately 1.30 and 1.81 minutes in a UV spectrum scan of liquid chromatography of said extract on a Zorbax 1.8 µM particle rapid resolution C18 column (4.6 mm×50 mm, 1.8 µm) with a 100% mobile phase (A) water-formic acid (100:01, v/v/v) to 100% B acetonitrile-formic acid (100:0.1, v/v/v) during 35 minutes and major peaks at approximately 1.61, 30.18, and 30.87 in a mass spectometry 100-1000 Mw in negative mode scan of liquid chromatography of said extract on a Zorbax 1.8 μM particle rapid resolution C18 column (4.6 mm×50 mm, 1.8 μm) with a 100% mobile phase (A) water-formic acid (100:0.1, v/v/v) to 100% B acetonitrile-formic acid (100:0.1, v/v/v) during 35 minutes, and wherein said extract inhibits platelet aggregation in an in vitro platelet aggregation assay.

DEFINITIONS

Figure 1:
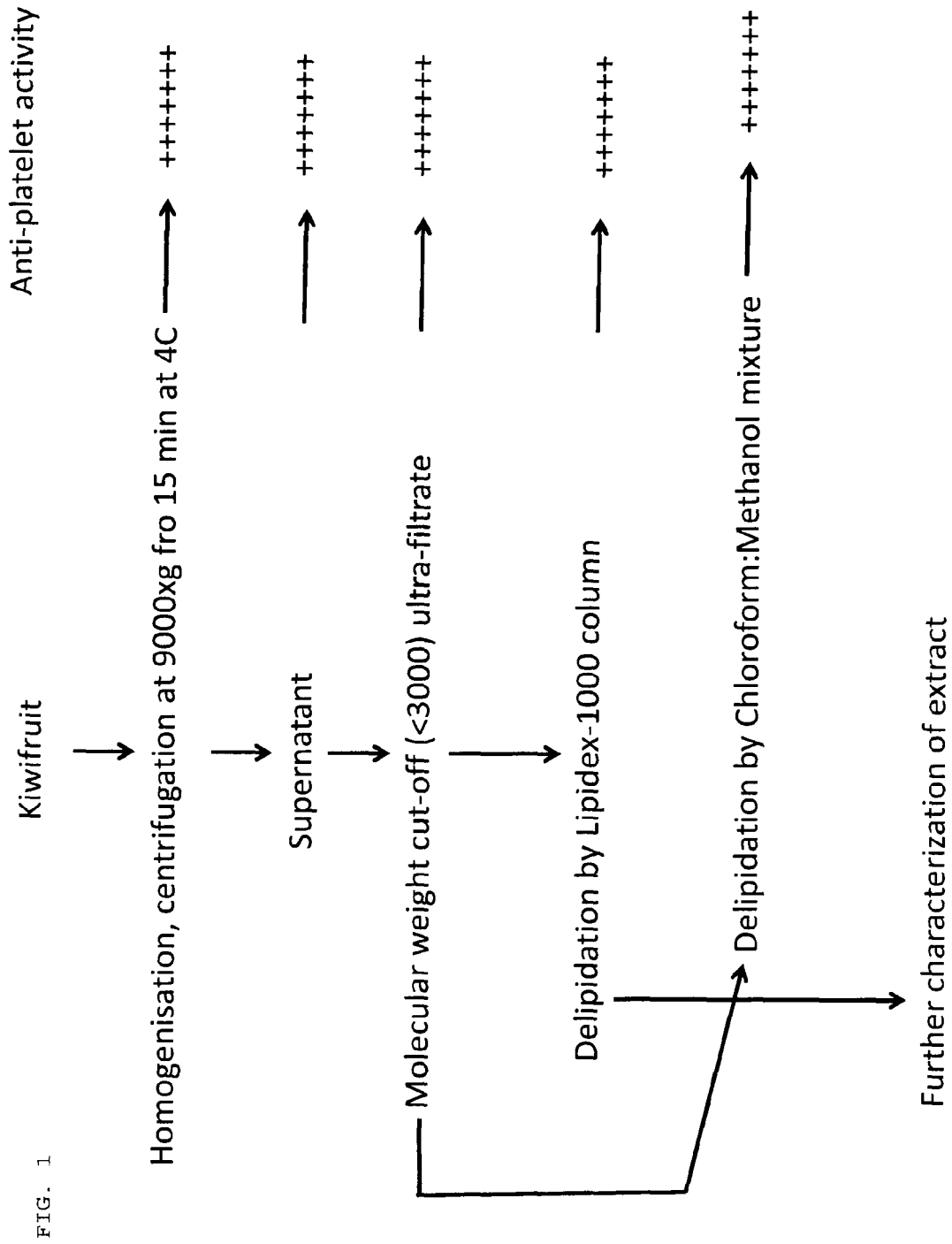
FIG. 1 shows in schematic from a procedure for partial fractionation of kiwi fruit extracts.

As used herein the term 'fraction' refers to a partially purified extract or compounds purified from an extract.

The term "purified" or "to purify" means the result of any process that removes some of a contaminant from the component of interest, such as the components responsible for inhibition of platelet aggregation. The percent of a purified component is thereby increased in the sample.

As used herein, the term "physiologically acceptable carrier" refers to any carrier or excipient commonly used with oily pharmaceuticals. Such carriers or excipients include, but are not limited to, oils, starch, sucrose and lactose.

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed). "Prepared food product" means any pre-packaged food approved for human consumption.

As used herein, the term "foodstuff" refers to any substance fit for human or animal consumption.

As used herein, the term "functional food" relates to any fresh or processed food claimed to have a health-promoting and/or disease-preventing property beyond the basic nutritional function of supplying nutrients. Functional foods are sometimes called nutraceuticals. The general category includes processed food made from functional food ingredients, or fortified with health-promoting additives, like "vitamin-enriched" products, and also, fresh foods (e.g., vegetables) that have specific claims attached. Fermented foods with live cultures are often also considered to be functional foods with probiotic benefits.

As used herein, the term "nutritional supplement" refers to a food product formulated as a dietary or nutritional supplement to be used as part of a diet.

DETAILED DESCRIPTION OF THE INVENTION

The invention relates to cardio-protective agents. In particular, the present invention relates to cardio-protective extracts and fractions thereof prepared from kiwi fruit.

Kiwifruit is the most well-known crop in the genus *Actinidia* (3). Although *Actinidia* fruit sales in the international market are dominated by a single kiwifruit cultivar *Actinidia deliciosa* "Hayward," there are a considerable number of cultivars and selections in the genus that have widely diverse shape, size, and hairiness. They also offer a wide variation in sensory attributes such as flesh color, flavor, and taste, and in nutritional attributes such as the vitamin C level, polyphenols, and carotenoid content (4,5). Few types of processed kiwifruit food products are commercially available to consumers. Kiwifruits are mainly eaten as whole fruits. The few examples where kiwifruit has been processed into products include frozen desserts and blended juices and more recently a few natural kiwifruit drinks such as Kiwi Crush™ (Vital Food Processors Ltd, Manukau City, Auckland, New Zealand). Kiwifruit extracts containing the fruit's nutritional components and desirable bioactives, including polyphenols, ascorbic acid and water-soluble polysaccharides (pectic polysaccharides), which may be advantageous for functional food applications, increasing the range of kiwifruit products available to consumers (3). With growing health awareness, there are increased consumer demands for acceptable nutritional foods with multiple consumer benefits including defined health benefits, increased convenience and reduced additives.

Platelets are involved in the development of atherosclerosis, and thrombotic events, and therefore reduction of platelet activity by medications reduces the incidence and severity of disease (1). Experiments conducted during the course of development of embodiments of the present invention evaluated whether consuming kiwi fruit modulated platelet activity and plasma lipids in healthy human volunteers in a randomized crossover study. It was reported that consuming two or three kiwi fruits per day for 28 days reduced platelet aggregation response to collagen and ADP by 18% compared with the controls (6). In addition, consumption of kiwi fruits lowered blood triglycerides levels by 15% compared with control, whereas no such effects were observed in the case of plasma cholesterol levels. All these data indicate that consuming kiwi fruit is beneficial in cardiovascular disease. Incubation of kiwi fruit extract (KFE; expressed as weight of pulp used to prepare KFE) inhibited platelet aggregation but was not an optimal preparation as it requires a good amount of flesh plus the activity can be lost in storage even at 4 degrees C. due to unwanted reactions in the juice. In addition, it is thought that tannins and oil in the seeds (and to a lesser extent the hair) can react with the highly acidic pulp to give rise unwanted smell and colour. Many kiwifruit species have a fine hair which is difficult to remove from a juice. Soft-pulping methods are preferred as it is considered desirable to avoid both excessive cell disintegration and fragmenting components of the fruit such as the seed. Seeds may contain toxic substances (e.g. apricot kernel) or contribute to off or undesirable flavors in a juice.

Many fruits are acidic and those with a pH of 6 or less are generally most likely to be affected. Widely used and relatively inexpensive sucrose is alkaline and appears to induce or take part in further undesirable reactions when added to an acidic pulp. Research leading to embodiments of the present invention indicated that substances entering a juice from seed fragmentation or excessive cell damage contribute to factors adversely affected the production of successful kiwifruit juice, such as problems of browning and catch factor. The kiwifruit is more acidic than most and has a pH of approximately 3. This may also avoid any possible side reactions contributing to catch, discoloration etc. Glucose and fructose are commonly found in many fruits. Typically this is by masking some of the undesirable properties of fruit such as bitterness or excess acidity and is due partly to the average human's affinity for sweetness. In some embodiments, juice products have not been pasteurized as characteristic of most other juices and processes. Hence any preservative effects which are contributed by the sweetening agent will help prolong the shelf life of the product. It is possible that the alteration in pH resulting from the combination may cause unwanted side reactions. Furthermore, it is noted that under storage, the chemistry of most juices will vary. For kiwifruit, the acid content of the juice will drop. Accordingly, in some embodiments the addition of a suitable buffering or pH adjusting agent help to preserve the pH of the product over a longer period. This also defers any undesirable long term reactions resulting in browning or discoloration of the juice.

In some embodiments, the active fractions of fruit, and in particular kiwifruit, are utilized in a variety of formulations and are preferably added to any matrix for human consumption that as are known in the art. In some preferred embodiments, the active fractions are characterized in having high efficacy for a particular use, such as prevention of platelet aggregation or adhesion, as being substantially free from inactive materials, as having an enhanced shelf-life as compared to untreated active fractions. In some embodiments, the fractions are produced by a process where a juice or pulp fraction is centrifuged, filtered, and delipidated to provide highly enriched platelet inhibitors (i.e., more than 10, 20, or 30 fold and up to about 50 fold or 100 fold as compared with raw, unprocessed juice). This process produces an active fraction with an enhanced shelf-life and which is stable to heating. In some preferred embodiments, the active fraction is heat-treated to further enhance stability. In further embodiments, there is provided a reconstituted product from an active fraction as described above. The present invention has been developed for members of the genus *Actinidia*. Fruit products, other than a juice, are also within the scope of embodiments of the invention. These fruit generally have a low pH (3.0-3.5), suffer from browning upon exposure of a juice to air and have a chlorophyll content. It is envisaged that while the process of the invention will be amenable to other fruit, the greatest advantage is likely to be realized for fruit suffering problems and characteristics in common with the kiwifruit e.g. a pH of less than 4.5, significant chloroplast levels, or catch (e.g. the fruit of *Monstera deliciosa*). It should not be inferred that benefit from the invention is limited to these types of fruit.

The invention has identified several problem areas, especially for kiwifruit, and addresses their needs.

Experiments conducted during the course of developments of embodiments of the present invention demonstrated that the KFE exhibits an ability to inhibit platelet aggregation, and reduce angiotensin converting enzyme (ACE) activity in vitro. The results obtained to date indicate that compositions containing KFE are of use in preventing cardiovascular disease, for example myocardial infarctions, and stroke and in preventing further thrombo-embolic events in patients who have suffered myocardial infarction, stroke or unstable angina. In addition such composition is of use in preventing restenosis following angioplasty and bypass procedures. Moreover KFE is of use in the treatment of coronary disease resulting from thrombo-embolic disorders such as MI in conjunction with thrombolytic therapy. Results obtained to date indicate that compounds responsible for anti-platelet aggregation activity are water soluble compounds having a very different structure to the lipid soluble compounds. There are many known anti-platelet aggregating agents that act different stages platelet production and action. Aspirin (acetylsalicylic acid) is the most widely used and studied. Dipyridamole and ticlopidine have also been used. Aspirin's anti-platelet activity is due to irreversible inhibition of platelet cyclooxygenase, thus preventing the synthesis of thromboxane $A_2$, a compound that causes platelet aggregation. Ibuprofen is a reversible inhibitor of platelet cyclooxygenase. Some compounds are direct inhibitors of thromboxane $A_2$ synthetase, for example pirmagrel, or act as antagonists at thromboxane receptors, for example sulotroban.

The present invention is not limited to a particular mechanism. Indeed, an understanding of the mechanism is not necessary to practice the present invention. Nonetheless, the results described herein indicate that the active components in the fruit extract may affect one or more steps of the pathways leading to the production of thromboxane $A_2$ upstream from that of aspirin and other anti-platelet drugs currently available. It is well known that the adverse effects are common occurrences with therapeutic doses of aspirin; the main effects being gastro-intestinal disturbances such as nausea, dyspepsia, and vomiting. It is anticipated therefore that the isolated platelet aggregation inhibition compounds in fruit extract find use in as a desirable alternative to aspirin and other anti-platelet drugs in the prevention of thrombo-embolic events and coronary disease.

Accordingly, in some embodiments, the invention provides a fruit extract, active fraction thereof, or one or more active compounds isolatable therefrom, for use in the prophylaxis or treatment of a disease state initiated or characterized by platelet aggregation.

In further embodiments, the invention provides a fruit extract or active fraction thereof or one or more compounds isolatable thereof for use as an anti-thrombotic agent.

In still further embodiments, the invention provides a fruit extract or active fraction thereof or one or more compounds isolatable thereof as here in before defined for the manufacture of a medicament for use in the prophylaxis or treatment of a disease state initiated or characterized by platelet aggregation; or for use as a platelet aggregation inhibitor: or for use an anti-thrombotic agent.

In some embodiments, the invention provides a process for the manufacture of a medication for use (i) in the prophylaxis or treatment of a disease state initiated, mediated or characterized by platelet aggregation, or (ii) as a platelet aggregation inhibitor, or as (iii) an anti-thrombotic agent: which process is characterized by the use, as an essential ingredient of the medicament, of a fruit, or an extract or active fraction thereof or one or more active components isolatable thereof as hereinbefore defined.

In some embodiments, the invention provides a pharmaceutical composition comprising an active component derived from a fruit or an extract or active fraction or one or more active compounds isolatable thereof as hereinbefore defined and pharmaceutically acceptable carrier.

In some embodiments, the invention provides a fruit extract, active fraction thereof, or one or more active compounds isolatable therefrom, for use in supporting cardiovascular health.

In some embodiments, the invention provides a fruit extract, active fraction thereof, or one or more active compounds isolatable therefrom, for use in supporting heart health.

In other embodiments, the invention provides a fruit extract or active fraction thereof or one or more compounds isolatable thereof for use as a platelet aggregation inhibitor.

In other embodiments, the invention provides a fruit extract or active fraction thereof or one or more compounds isolatable thereof for use in promoting or maintaining heart health and/or circulatory health.

In other embodiments, the invention provides a fruit extract or active fraction thereof or one or more compounds isolatable thereof for use in improving, maintaining and or promoting blood flow, and in particular the smooth flow of blood.

It is preferred that the fruit extract used in accordance with the invention are those which are non toxic to humans and typically the fruits which are usually considered to be edible fruits. Thus the fruits may or may not contain seeds or stones but have an edible essentially non-oily flesh.

Kiwifruit is the most well-known crop in the genus *Actinidia*. The extracts of embodiments of the invention can be prepared by homogenising the flesh of a peeled kiwifruit and then removing solids therefrom, for example by means of centrifugation. Thus the extract is a typically an aqueous extract, which can consist or comprise the juice of the fruit, optionally with the addition of extra water added during the homogenising step. Such aqueous extracts can be concentrated, enriched or condensed by, for example, standard techniques, e.g. evaporation under reduced pressure. Examples of concentrates are those which are at least 2-fold concentrated, more usually, at least 4-fold, for example at least 8-fold, or at least 40-fold or at least 100-fold or at least 200 fold or at least 1000 fold.

The extract can be fractionated to isolate one or more active fractions therein by, for example, molecular weight filtration, or chromatography on suitable support such as sepharose gel (for size exclusion chromatography) or removal of lipids (by Lipidex-1000) or by solvent treatments, or ion exchange column using HPLC on a suitably treated silica or alumina, for example ODS coated silica, or solvent extraction.

Experiments carried out on kiwi fruit extract have revealed that the active components of the extract passes through an ultrafiltration having molecular weight cut-off of 1000 is colorless, water soluble and does not lose activity when boiled. In some embodiments, the present invention provides a process for producing a stable and biologically active *Actinidia* extract comprising fractionating juice from an *Actinidia* fruit to produce an extract fraction and heating the extract fraction to about 70 to about 120 degrees Celsius, preferably 80 to 100 degrees Celsius, and most preferably to about 95 to 100 degrees Celsius. In some embodiments, the duration of the heating is from about 5 to about 30 minutes, preferably about 10 to about 25 minutes, and most preferably about 20 minutes, or more for more than about 5, 10, or 15 minutes. In some embodiments, the present invention provides a process for producing a stable and biologically active *Actinidia* extract comprising fractionating juice from an *Actinidia* fruit to produce an extract fraction and subjecting the fraction to ultrafiltration with a molecular weight cutoff of less than 10 kDa, preferably less than 5 kDa, and more preferably less than about 3 kDa, 2 kDa or 1 kDa. In some embodiments, the stabilized active fraction comprises biologically active molecules and is characterized in retaining at least 80% of biological activity of said biologically active molecules when stored for at least 4 days, 18 days or 24 days up to about 30 or 40 days at 4 degrees Celsius as compared to a fresh extract fraction. In some embodiments, the biological activity is inhibition of platelet aggregation in an in vitro platelet aggregation assay or inhibition of angiotensin converting enzyme activity.

In some preferred embodiments, the stable and biologically active *Actinidia* extract produced by this method exhibits major peaks at approximately 1.30 and 1.81 minutes on a UV spectrum chromatogram and major peaks at approximately 1.61, 30.18, and 30.87 on a total ion current chromatogram and wherein said extract inhibits platelet aggregation in an in vitro platelet aggregation assay.

Accordingly, embodiments of the invention also provides for use an antithrombotic agent, or for use as a platelet aggregation inhibitor, or for use in the prophylaxis or treatment of a disease state initiated or characterized by platelet aggregation, an active fraction of a fruit extract (e.g., kiwifruit extract) the active fraction containing a substantially heat stable colorless or slightly straw colored water soluble compounds with a molecular weight less than 3000, 2000, or 1000 kDa. In some embodiments, the active fraction is characterized as having a biologically activity. In some embodiments, the biological activity is an inhibition or decrease of angiotensin converting enzyme (ACE) activity by at least 5%, 10% or preferably 15% as compared to a control or placebo substance when the active fraction is incubated with normal serum for 10 minutes. In some embodiments, the biological activity is inhibition of platelet aggregation in an in vitro platelet aggregation assay. In some embodiments, the platelet aggregation inhibition is expressed as a percent inhibition of platelet aggregation by a known effector of platelet aggregation, for example collagen, ADP, or arachidonic acid. In some embodiments, the active fraction of the present invention inhibits platelet aggregation by one of these known effectors by at least 10%, 20%, 30% 40% or 50% up to about 50% or 60% as compared to a control or placebo substance.

The active fraction has been found to be primarily associated with, or extractable from, the juice, the flesh surroundings the pips and the pips of the kiwifruit. Thus, the use of compositions prepared from an active fraction consisting essentially of or comprising a homogenate or an extract thereof derived from the flesh of a peeled kiwifruit or consisting essentially of or comprising the juice and/or the flesh surrounding the pips, and or the pips, represents a preferred embodiment of the invention.

Accordingly, embodiments of the present invention provide an active fraction of a kiwifruit extract with one or more of the following characteristics:
  a) The size of molecules in the active fraction is less than 3000 kDa, and preferably less than 2000 kDa or 1000 kDa;
  b) The active fraction is substantially heat stable;
  c) The active fraction is substantially colorless;
  d) The active fraction substantially comprises water soluble compounds;
  e) The active fraction inhibits platelet aggregation; and
  f) The active fraction inhibits angiotensin converting enzyme The active fractions of the present invention may be provided in a variety of forms and in a variety of formulations. In some embodiments, the fractions are provided in as a liquid, a syrup, a powder, a paste, an emulsion, a pelleted composition, a granulated composition, an encapsulated composition, a suspension, a concentrate, a solution, and a lozenge. The powders may preferably be a lyophilized, freeze dried or spray dried powder prepared from the stabilized kiwi extract with or without a organoleptically and/or pharmaceutically acceptable excipient. The syrups may preferably be a viscous, concentrated aqueous solution prepared from the stabilized kiwi extract and may include suitable excipients and/or sweeteners. The syrups may be utilized for direct oral administration or as a concentrate for reconstitution with water prior to administration.

The fractions may be provided by any of a number of routes, including, but not limited to, oral, intravenous, intramuscular, intra-arterial, intramedullary, intrathecal, intraventricular, transdermal, buccal, subcutaneous, intraperitoneal, intranasal, enteral, topical, sublingual or rectal means. For details on techniques for formulation for and administration and administration may be found in the latest edition of Remington's Pharmaceutical Sciences (Maack Publishing Co., Easton, Pa.).

In some embodiments, the present invention provides an oral delivery vehicle comprising a fraction of the present invention. The fractions may preferably be formulated with pharmaceutically acceptable carriers such as starch, sucrose or lactose in tablets, pills, dragees, capsules, gel capsules, solutions, liquids, slurries, suspensions and emulsions. The tablets or capsules of the present invention may be coated with an enteric coating which dissolves at a pH of about 6.0 to 7.0. A suitable enteric coating which dissolves in the small intestine but not in the stomach is cellulose acetate phthalate. In some embodiments, the oral delivery vehicle comprises an amount of the first and second components effective to cause an effect in subject selected from the group consisting of increasing efficiency of muscle work, decreasing energy cost of work, increasing time of work to exhaustion, increasing endurance during physical exercise, increasing well-being, ameliorating muscle soreness after strenuous exercises, improving metabolic conditions in subjects with obesity and/or metabolic syndrome, and combinations thereof. Examples of improving metabolic conditions in subjects with obesity and/or metabolic syndrome include, but are not limited to, increasing glucose uptake, lowering oxidative stress, and combinations thereof. In some embodiments, the oral delivery vehicle comprises an effective amount of the fractions. In some embodiments, the effective amount comprises an amount of extract containing the biologically active ingredients found in from about 1 to about 20 kiwifruits, and preferably from about 1 to about 10 kiwifruits, and most preferably about 1 to 5 kiwifruits. In other embodiments, the effective amount corresponds to about 1 to about 5000 mg of the lyophilized or spray dried, stabilized fraction, preferably from about 1 to about 3000 mg of the lyophilized or spray dried, stabilized fraction and most preferably about 1 mg to about 1000 mg of the lyophilized or spray dried, stabilized fraction. In other embodiments, the effective amount corresponds to about 500 to about 20000 mg of the concentrated (e.g., as syrup), stabilized fraction, preferably from about 500 to about 10000 mg of the concentrated (e.g., as syrup), stabilized fraction and most preferably about 500 mg to about 2500 mg of the concentrated (e.g., as syrup), stabilized fraction.

In some embodiments, the present invention provides dietary supplements comprising the fractions of the present invention. The ingredients of the dietary supplement of this invention are preferably contained in acceptable excipients and/or carriers for oral consumption. The actual form of the carrier, and thus, the dietary supplement itself, is not critical. The carrier may be a liquid, gel, gelcap, capsule, powder, solid tablet (coated or non-coated), tea, or the like. The dietary supplement is preferably in the form of a tablet or capsule and most preferably in the form of a soft gelatin capsule. In other embodiments, the supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food. In preferred embodiments, the dietary supplements comprise an effective amount of the components as described above.

The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the dietary supplement of the present invention may contain one or more of the following: asorbates (ascorbic acid, mineral ascorbate salts, rose hips, acerola, and the like), dehydroepiandosterone (DHEA), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), *spirulina*, zinc, docosahexaenoic acid and/or eicosapentaenoic acid (provided in any form such as free fatty acids, trigylcerides or phospholipids) and the like. Such optional ingredients may be either naturally occurring or concentrated forms.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin $D_3$, cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In preferred embodiments, the dietary supplements comprise an effective amount of the fractions as described above. The dietary supplements of the present invention may be taken one or more times daily. Preferably, the dietary supplement is administered orally one to two times daily. Frequency of administration will, of course, depend on the dose per unit (capsule or tablet) and the desired level of ingestion. Dose levels/unit can be adjusted to provide the recommended levels of ingredients per day (e.g., an effective amount as described above) in a reasonable number of units (e.g., two capsules or tablets taken twice a day). In preferred embodiments, the doses add up each day to the daily intake of each ingredient. In preferred embodiments, the dietary supplements are taken with meals or before meals. In other embodiments, the dietary supplements are not taken with meals.

In other embodiments, the present invention provides nutritional supplements (e.g., energy bars or meal replacement bars or beverages) comprising of the fractions of the present invention. In preferred embodiments, the nutritional supplements comprise an effective amount of the components as described above. The nutritional supplement may serve as meal or snack replacement and generally provide nutrient calories. Preferably, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties.

Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g., sucrose, maltodextrins, and uncooked cornstarch).

Sources of protein to be incorporated into the nutritional supplement of the invention can be any suitable protein utilized in nutritional formulations and can include whey protein, whey protein concentrate, whey powder, egg, soy flour, soy milk soy protein, soy protein isolate, caseinate (e.g., sodium caseinate, sodium calcium caseinate, calcium caseinate, potassium caseinate), animal and vegetable protein and mixtures thereof. When choosing a protein source, the biological value of the protein should be considered first, with the highest biological values being found in caseinate, whey, lactalbumin, egg albumin and whole egg proteins. In a preferred embodiment, the protein is a combination of whey protein concentrate and calcium caseinate. These proteins have high biological value; that is, they have a high proportion of the essential amino acids. See Modern Nutrition in Health and Disease, eighth edition, Lea & Febiger, publishers, 1986, especially Volume 1, pages 30-32.

The nutritional supplement can also contain other ingredients, such as one or a combination of other vitamins, minerals, antioxidants, fiber and other dietary supplements (e.g., protein, amino acids, choline, lecithin, other fatty acids). Selection of one or several of these ingredients is a matter of formulation, design, consumer preference and end-user. The amounts of these ingredients added to the dietary supplements of this invention are readily known to the skilled artisan. Guidance to such amounts can be provided by the U.S. RDA doses for children and adults. Further vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin $D_3$; cyanocobalamin; sodium selenite; copper sulfate; vitamin A; vitamin C; inositol; potassium iodide.

Flavors, coloring agents, spices, nuts and the like can be incorporated into the product. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the final product. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product.

Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutritional supplement can contain natural or artificial (preferably low calorie) sweeteners, e.g., saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycemia.

The nutritional supplement can be provided in a variety of forms, and by a variety of production methods. In a preferred embodiment, to manufacture a health bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

In still further embodiments, the present invention provides food products, prepared food products, or foodstuffs comprising the extracts or fractions described above (i.e., functional foods). In preferred embodiments, the foods comprise an effective amount of the fractions as described above. For example, in some embodiments, beverages and solid or semi-solid foods comprising the extracts, fractions or derivatives thereof are provided. These forms can include, but are not limited to, beverages (e.g., soft drinks, milk and other dairy drinks, and diet drinks), baked goods, puddings, dairy products, confections, snack foods, or frozen confections or novelties (e.g., ice cream, milk shakes), prepared frozen meals, candy, snack products (e.g., chips), soups, spreads, sauces, salad dressings, prepared meat products, cheese, and yogurt.

EXPERIMENTAL

The following examples are provided in order to demonstrate and further illustrate certain preferred embodiments and aspects of the present invention and are not to be construed as limiting the scope thereof.

Example 1

Preparation of Kiwifruit Extract:

Extract consisting of 100% kiwifruit juice was prepared. To prepare 100% fruit juice, the fruits were peeled and the flesh was homogenized. The resulting homogenate was spun at 9000×g for 15 min at 4° C. on a centrifuge after which the supernatant was removed and the pH of the juice was adjusted to 7.4 with 1M sodium hydroxide solution. The anti-platelet activity of the kiwi fruit extract (KFE) was determined initially.

Partial Fractionation of Kiwi Fruit Extract:

Kiwifruit extracts were then fractionated according to the general scheme set out in FIG. 1. The platelet aggregation inhibiting activity of the preparations was measured at various stages. Thus, fresh kiwifruit juice, prepared from 100% fruit, was centrifuged at 9000×g for 10 min. Following centrifugation, the supernatant was freeze dried and a portion of the dried material was dissolved in phosphate buffer and pH was adjusted to 7.4. This was then subjected to ultrafiltration by passing through filter with molecular weight cut-off 1000 dalton. The ultrafiltrate was collected, and freeze dried and reconstituted in water, and pH was adjusted to 7.4. The platelet aggregation was measured using the extract at different stages of fractionation (FIG. 1). In a separate study, the extract was boiled for 10 min. and centrifuged, and the anti-platelet activity of the boiled sample was determined.

In order to examine whether lipid compounds in the fractionated extracts were responsible for anti-platelet activity, the lipids of the extract were removed by passing the solution through the specially prepared Lipidex-1000 column (column volume 18 ml). Lipidex-1000 adsorps lipid substances of the extract only. The column was then eluted with 5 column volumes of 15 mM phosphate buffer, and the eluted solution was collected and dried. Lipid compounds bound to column resin were later eluted with methanolic solution and dried for anti-platelet activity measurement.

Further to the above Lipidex-1000 experiment, the lipids were also removed with another method by using chloroform methanol according to the Bligh and Dyer. Thus, 2 ml of the ultrafiltrate were mixed with 2.5 ml of methanol followed by 1.25 ml chloroform to give a sing phase, and a chloroform:methanol:water ratio of 1:2:0.8. No precipitate was formed. Chloroform (1.25 mL) and water (1.25 mL) were then added and after gentle mixing, the mixture was allowed to settle into two layers. The upper layer (methanol/water) was removed and the methanol blown off under nitrogen at 55° C. The volume was then made up to 2 mL after adjustment to pH 7.4. The anti-platelet aggregation activity of this aqueous phase was compared with respective volume of phosphate buffer as a control.

The chloroform phase was then evaporated under nitrogen, and resuspended in ethanol (50 µL). A sample (10 µL) of the ethanol phase then tested for anti-platelet aggregation activity versus a 10 µL ethanol control.

Platelet Aggregation Study:

The effect of the fruit extracts on the aggregatory properties of human platelets was investigated by means of blood donated by healthy volunteers. Venous blood was collected from volunteers who had not taken any medications for at least 14 days before donation. Blood (20 ml) was collected using a 19G butterfly needle and coagulation was prevented by mixing the blood samples with acid citrate, (135 mM) in the ration of 9 parts by volume of blood up to 1 part by volume of acid citrate. Platelet rich plasma (PRP) was prepared from the samples by centrifuging the blood at 180×g from 15 min. Kiwi fruit juice (10-30 µl), the pH was adjusted to 7.4 with 1M sodium hydroxide was mixed with the PRP to make volume up to 500 µl, and incubated at 37° C. from 15 min. after which the effect of the fruit extract on ADP induced platelet aggregation was monitored with the addition of ADP to a final concentration 5 µM. Controls were run in parallel using 10-30 µL phosphate buffer, pH 7.4 instead of the fruit extract. Platelet aggregation in PRP was monitored using a Chrono-Log aggregation (Chrono-Log, USA) at a constant stirring speed of 1000 rpm at 37 C.

To determine the effect of KFE on platelet aggregation in vitro, PRP (450 µl) was incubated with different concentrations of KFE in volume 50 µl for 15 min at 37° C. prior to the addition of an aggregating agent. The $IC_{50}$ for different fractions of KFE was determined by incubating these platelets with different concentrations of KFE for 15 min. Controls were run in parallel replacing fruit extract with 50 µl of phosphate. Inhibition of platelet aggregation is expressed as the decrease in the area under the curve compared with the control.

Inhibition of Angiotensin Converting Enzyme (ACE) by KFE:

Angiotensin I-converting enzyme (ACE, EC 3.4.15.1), an exopeptidase, is a circulating enzyme that participates in the body's renin-angiotensin system, which mediates extracellular volume (e.g., that of the blood plasma, lymph and interstitial fluid), and arterial vasoconstriction. It is secreted by pulmonary and renal endothelial cells and catalyzes the conversion of decapeptide angiotensin I to octapeptide angiotensin II. ACE inhibitors block the conversion of angiotensin I to angiotensin II. They therefore lower arteriolar resistance and increase venous capacity; increase cardiac output and cardiac index, stroke work and volume, lower renovascular resistance, and lead to increased natriuresis (excretion of sodium in the urine). With ACE inhibitor use, the effects of angiotensin II are prevented, leading to decreased blood pressure. The effect of KFE on the serum ACE activity measured using Angiotensin Converting Enzyme Assay kit by BÜHLMANN LABORATORIES AG, Germany.

Results:

Fractionation of Kiwi Fruit Extracts and their Effects on ADP-Induced Platelet Aggregation by ADP.

FIG. 1 shows the preparation of kiwifruit extract using different fractionation procedures. The inhibitor(s) of platelet aggregation in kiwi extracts were present in the water soluble fraction and their size is smaller than 1000 daltons. Boiling of this fraction did not destroy the activity. Delipidation of the sample by Lipidex-1000 demonstrated that the active fraction is present in aqueous extract.

Platelet Aggregation Studies

Table 1 shows the dose response of KFE on inhibition of platelet aggregation by different agents. It demonstrated a dose response effect with ADP-induced aggregation: increasing the KFE led to greater reduction in platelet aggregation. The fraction isolated from kiwifruit was equally effective against all three platelet aggregating agents, collagen, ADP, and arachidonic acid.

Figure 2:
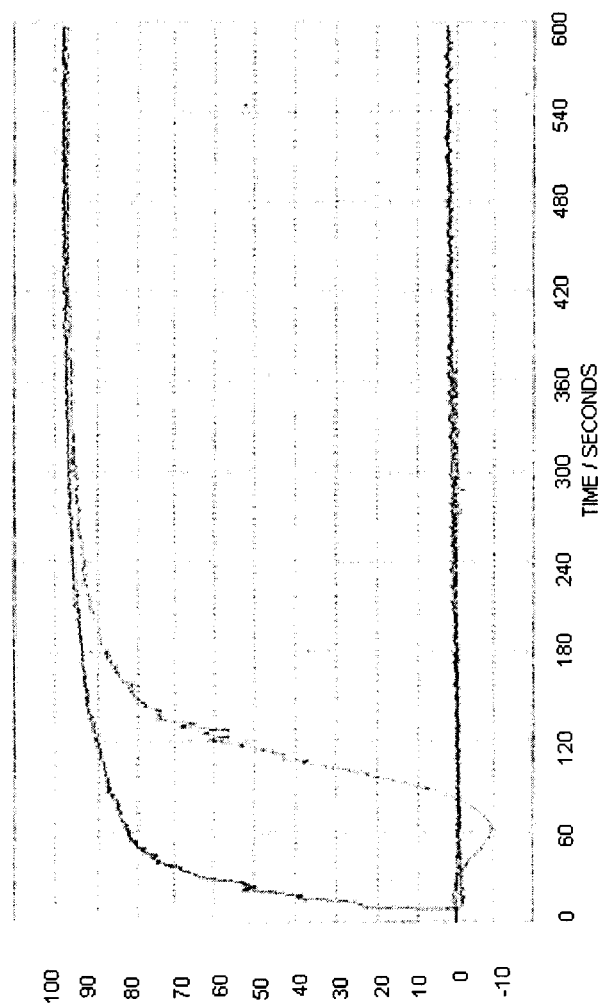
FIG. 2 shows platelet aggregation inhibition induced by ADP activity by the extract.

FIG. 2 shows the effect of different volumes of kiwi fruit extract on platelet aggregation by ADP in vitro. PRP (450 ml) was incubated with different volumes (0, 10, 20 and 30 ul) of KFE for 15 min at 37 C prior to the addition of agonists, arachidonic acid (500 µg/ml), ADP (3 mM, and collagen (1 µg/ml). KFE inhibited ADP-induced aggregation in a dose dependent manner (Table-1). ADP induced aggregation was inhibited by 45% with 10 µl KFE, 65% with 20 µl KFE, and 95% with 30 µl KFE, compared with controls.

Similarly, KFE inhibited collagen induced platelet aggregation; the level of inhibition was lower with 10 and 20 µl incubations. Inhibition of arachidonic acid-induced platelet aggregation exhibited 38% inhibition at the highest KFE level tested and very little inhibition at lower concentrations of KFE.

TABLE 1

| Kiwifruit extract | Inhibition of platelet aggregation by three different agonists (mean %) | | |
|---|---|---|---|
| Volume (µl) | Arachidonic acid | Collagen | ADP |
| 10 | 12 | 18 | 45 |
| 20 | 25 | 45 | 65 |
| 30 | 38 | 90 | 95 |

Boiling of kiwifruit extract at 100 C for 10 min did not affect anti-platelet aggregation of the extract.

Determination of the Effect of KFE on Platelet Aggregation Induced by Different Agonists.

Figure 3:
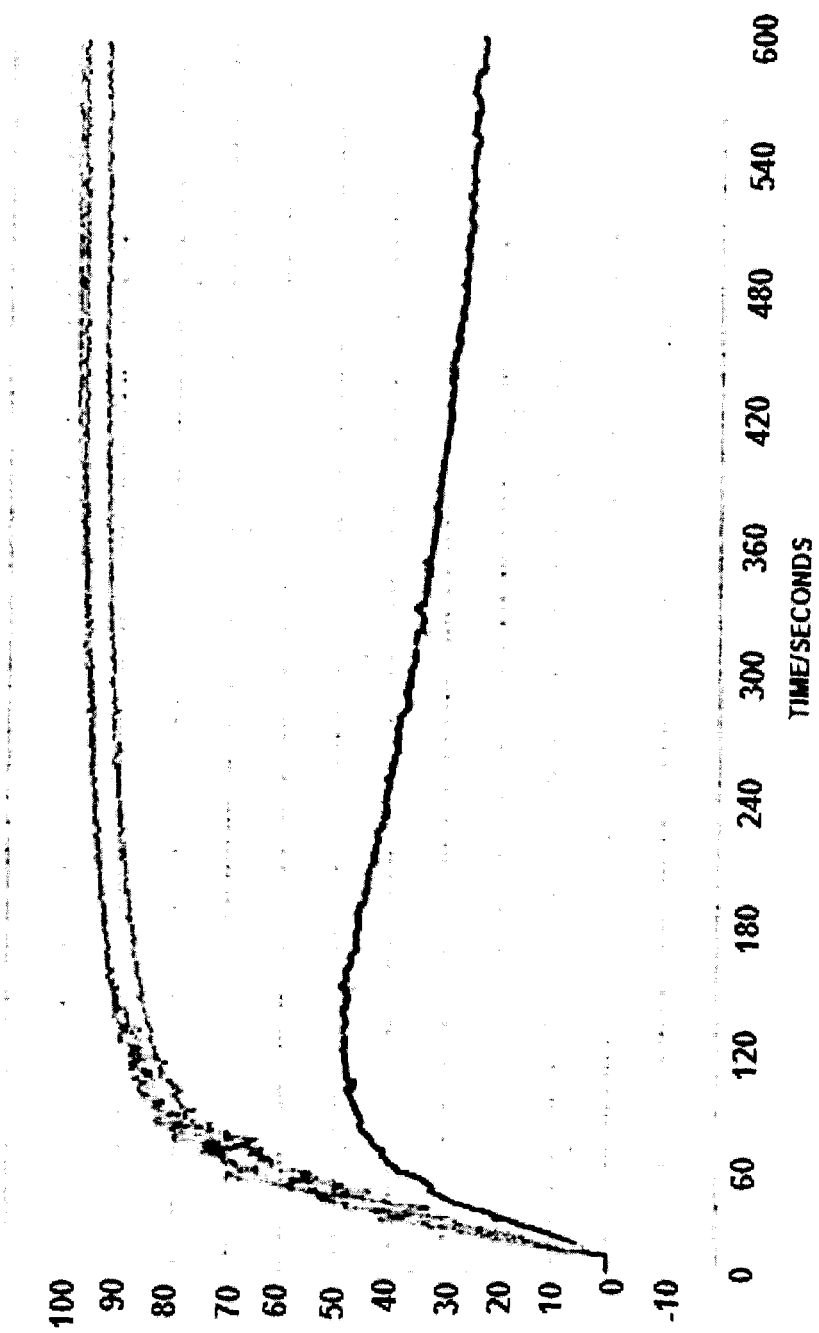
FIG. 3 shows the inhibition of platelet aggregation induced by arachidonic acid.

FIGS. 2 and 3 show the inhibition of platelet aggregation induced by collagen and arachidonic acid, respectively. The experimental conditions are described in Table-1.

Determination of the Effect of Fractionated Kiwifruit Extract on Platelet Aggregation Induced by ADP.

Figure 4:
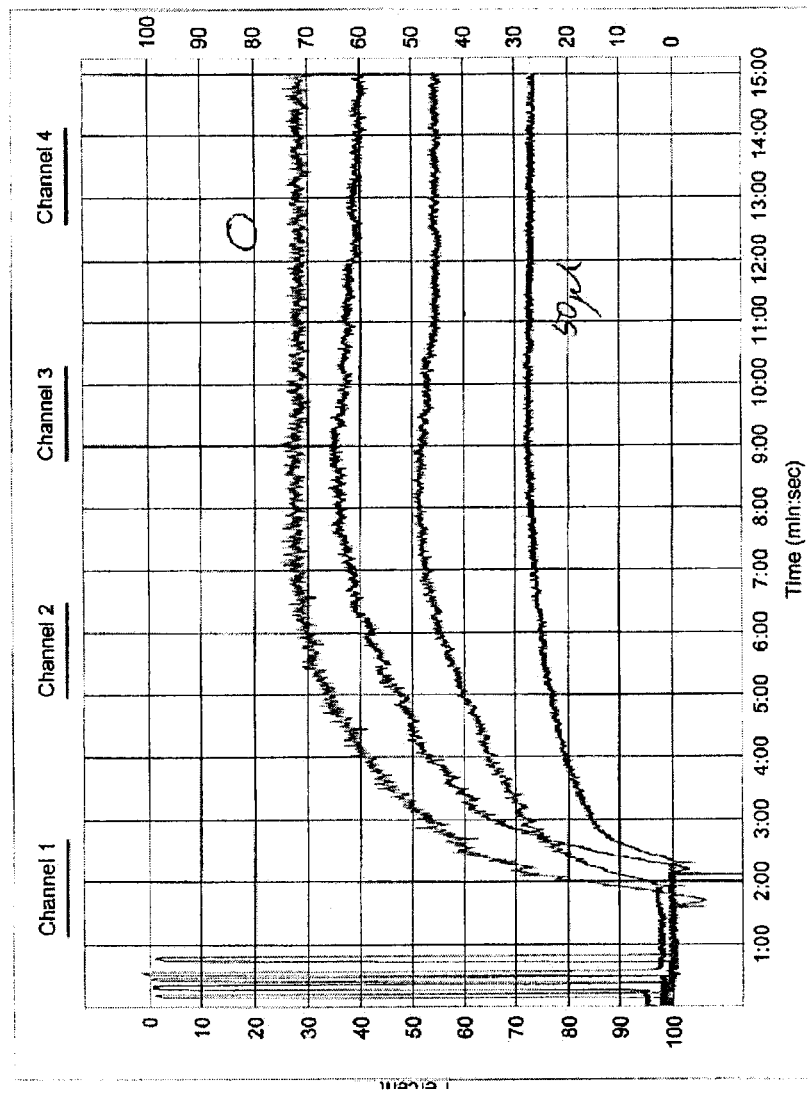
FIG. 4 shows the effects of KFE on ACE activity of human serum.

FIG. 4 shows the effect of fractionated kiwifruit extract on platelet aggregation induced by ADP. The experimental conditions are described in Table 1. KFE was purified as described in FIG. 1.

Effects of KFE on ACE Activity of Human Serum.

Incubation of serum with 20 µl of KFE for 15 min inhibited more than 15% activity compared with control.

Figure 5:
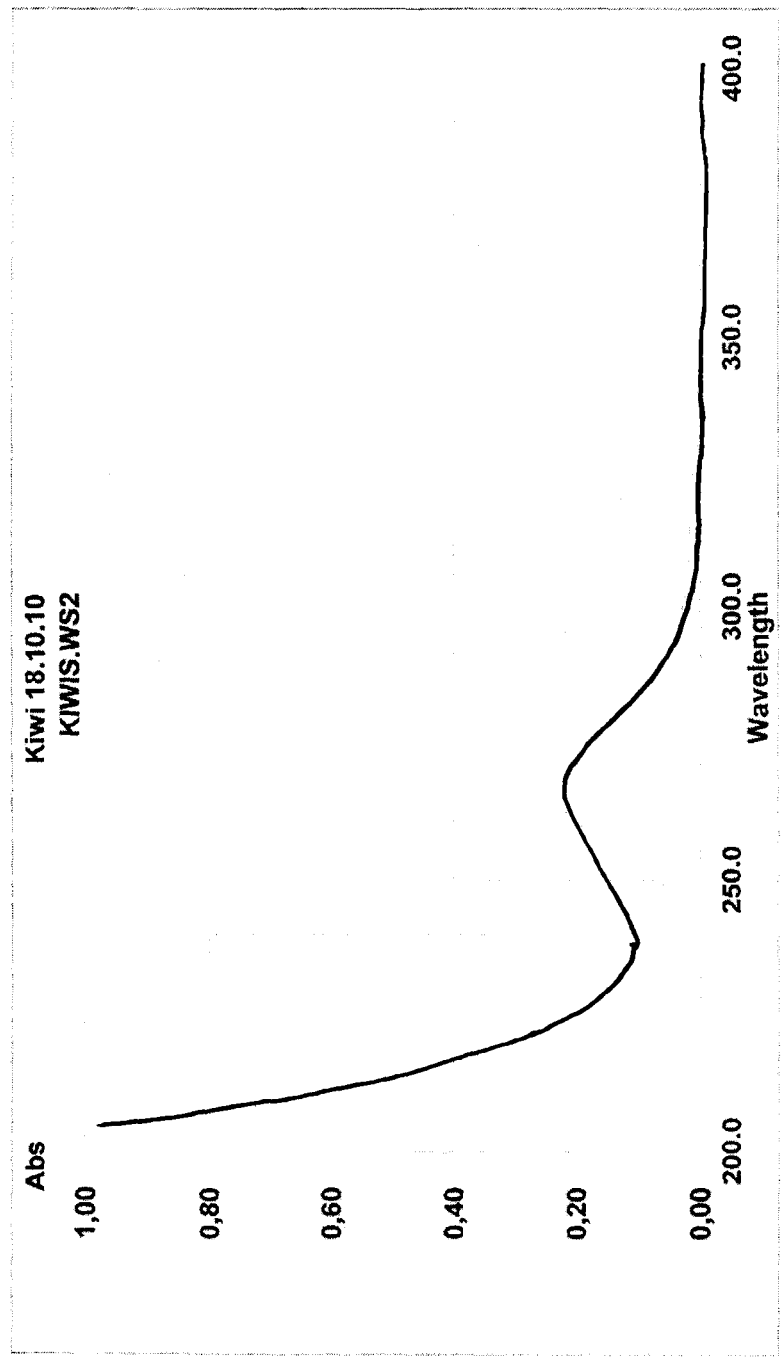
FIG. 5 shows UV scanning of a delipidated, ultrafiltrated purified fraction of kiwifruit extract (KFE).

FIG. 5 shows UV scanning of the delipidated, ultrafiltrated purified active fractions of the Kiwifruit extract.

Example 2

This example describes the UV and MS spectra of the highly purified heat stable and water soluble kiwi fruit extract that contains anti-platelet activity.

Figure 6:
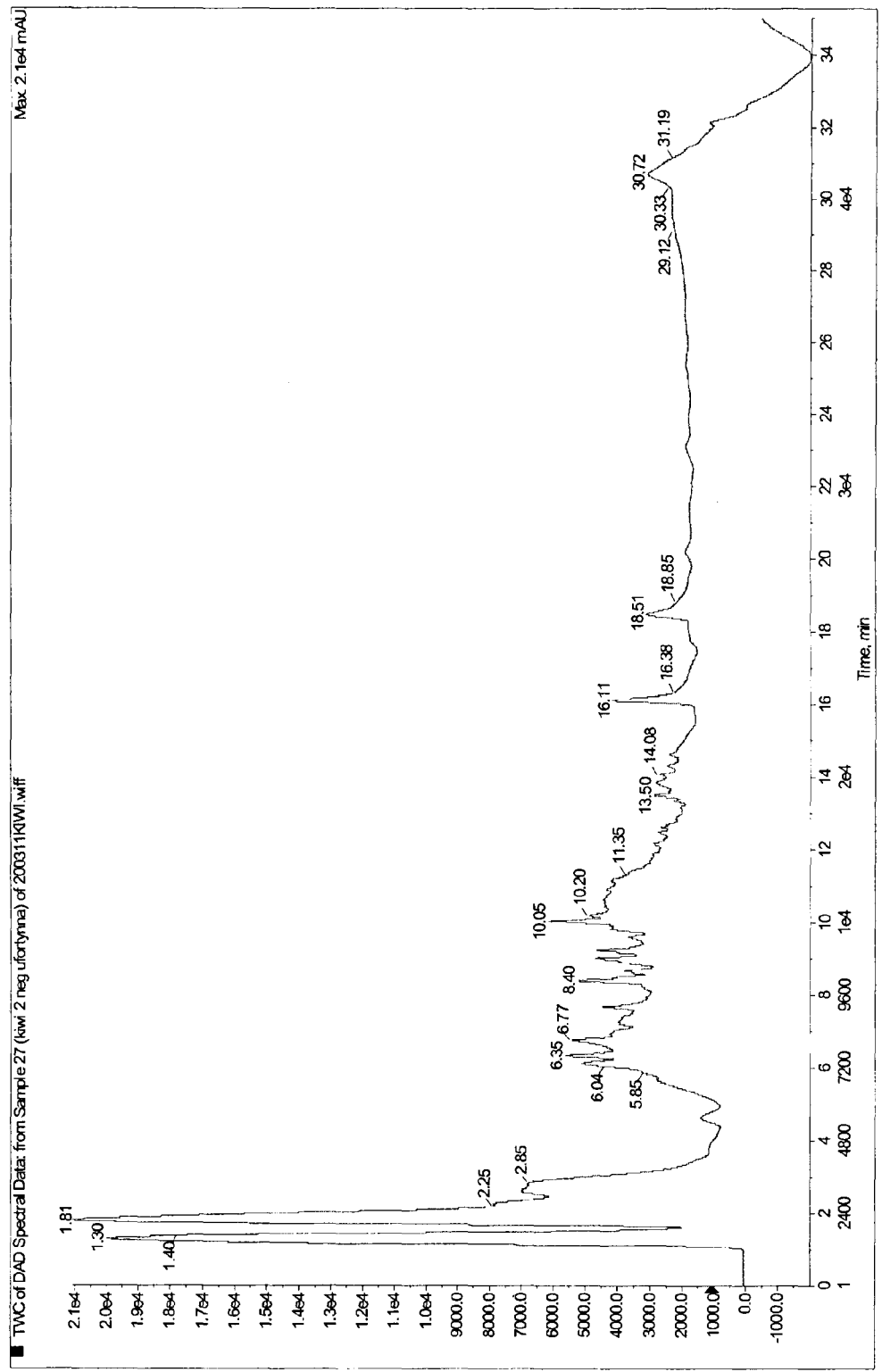
FIG. 6 provides a chromatogram of a UV spectral 200-400 nm scan of a kiwi extract of the present invention.
Figure 7:
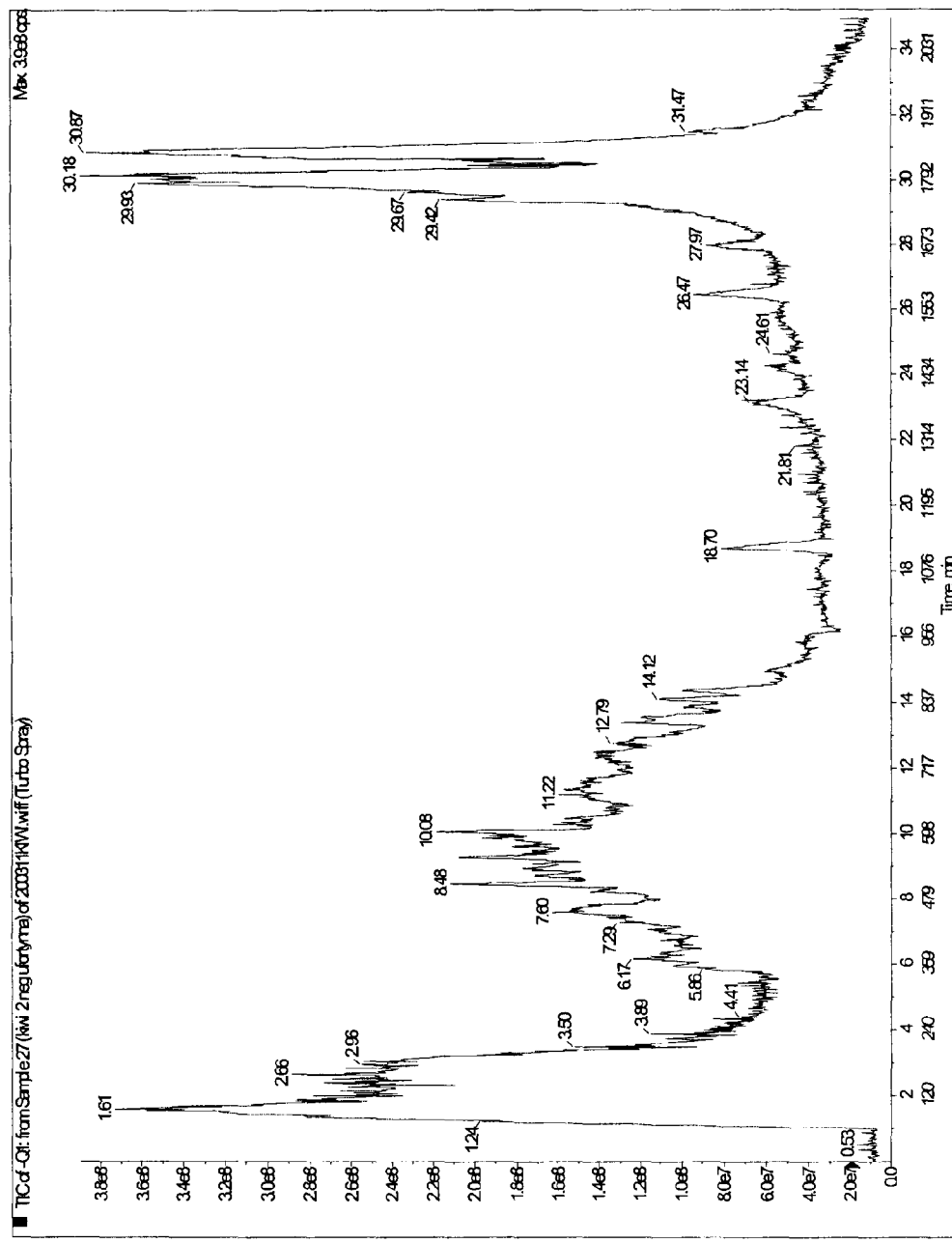
FIG. 7 provides a chromatogram of a MS scan 100-1000 Mw in negative mode of a kiwi extract of the present invention.

The kiwifruit juice was prepared and the juice was clarified by centrifugation at 9000 g for 15 min. The supernatant was then boiled at 90 C for 20 min. The cooled extract was then centrifuged again at 9000×g for 15 min. The colourless supernatant was then passed through LIPDEX-1000 column to remove any associated lipids. The eluted delipidated sample was then freeze dried and passed through the 1000 dalton molecular cut-off filter. The filtrate was then run in triple stage LC-MS/MS-UV. MS scans 100-1000 Mw in negative mode (FIG. 7) and UV spectral 200-400 nm (FIG. 6).

The column is a Zorbax 1.8 µM particle rapid resolution C18 column (4.6 mm×50 mm, 1.8 µm). Elution was accomplished by starting 100% mobile phase (A) water-formic acid (100:0.1, v/v/v) to 100% B acetonitrile-formic acid (100:0.1, v/v/v) during 35 minutes.

Example 3

Kiwifruit juice was prepared after homogenization of the peeled fruits, subsequently-centrifuged at 9000×g for 15 min and kept at 4 C for antiplatelet assay. The other fraction of juice was boiled-at 90 C for 20 min and centrifuged again, and pH was adjusted to 7.4 and kept at 4 C and kept up to 24 days. The anti-platelet activity of the juice and the extract was measured at different days by incubating the PRP with the juice (after adjusting pH to 7.4) or the extract for 15 min, and the inhibition was compared with control (in the absence of juice or extract) using 3 µM ADP as-an aggregating agent.

| Day | Kiwifruit Juice Inhibitory Activity | Kiwifruit extract Activity |
|---|---|---|
| Day 0 | 100 | 100 |
| Day 4 | 76 | 100 |
| Day 18 | 29 | 100 |
| Day 24 | 4 | 100 |

Conclusion: The juice lost activity by 24% within a week and 70% after 18 days, whereas the boiled extract retained 100% activity. The freeze-dried extract retained all activity Example 4

The kiwifruit extract was prepared as described before. The final preparation yield was 4-5 g per 100 g of fruits and that contained 45-50% sugar. The data presented here used the extract prepared in Trondheim. 20 gm of KFE was mixed with 200 ml of Tine Milk Orange juice for consumption. Six healthy adults of both sexes were recruited into the study. Subjects were aged 25-60 y and had no history of serious disease or hemostatic disorders. Suitability for inclusion into the study was assessed by using diet and lifestyle questionnaires and by medical screening, during which platelet function was assessed. Subjects were selected on the basis of high platelet function, as determined by the platelet aggregation response to 3 µmol ADP/L. Subjects habitually consuming dietary supplements (e.g., fish oils) were asked to suspend these supplements for a minimum of 1 month before participating in the study. Subjects were instructed to abstain from consuming drugs known to affect platelet function for a 10-d period before participation.

Written informed consent was obtained from all subjects. This study was approved by the Oslo authority. Volunteers were overnight fasted. Venous blood samples of ≈20 mL were drawn at each sampling time point (time 0) and then they were asked to drink 200 ml orange juice containing 20 g KFE. For measurements of platelet function blood was collected into plastic syringes and transferred into citrated blood collection tubes (final sodium citrate concentration, 13 mmol/L).

Ex vivo platelet aggregation studies Measurement of the extent of ADP-induced platelet aggregation in PRP was carried out at each time point. The platelet response to suboptimal ADP concentrations was also of interest; under these conditions, a biphasic aggregation response may be observed, which provides further information about the nature of the platelet response. A standardized r ADP concentration (3 µmol/L) was used for all measurements. For ex vivo studies, effects on platelet aggregation observed after treatment or control interventions are expressed as the percentage change in area under the aggregation curve after consumption of extract or placebo, as compared with baseline values.

The results are as here expressed as % inhibition

| Volunteers | % inhibition after 2 hours |
|---|---|
| 1 | 8.1 |
| 2 | 12.6 |
| 3 | 12 |

-continued

| Volunteers | % inhibition after 2 hours |
|---|---|
| 4 | 15 |
| 5 | 8.2 |

REFERENCES

1. Dutta-Roy A K. (2002) Dietary components and human platelet activity. Platelets. 13(2):67-75
2. Dutta-Roy, A K, Crossbi, L, and Gordon, M. J. (2001) Effects of tomato extract on human platelet aggregation in vitro, Platelets, 12(4):218-27.
3. Nishiyama I. Fruits of the *actinidia* genus. Adv Food Nutr Res. 2007; 52:293-324.
4. Sun-Waterhouse D, Chen J, Chuah C, Wibisono R, Melton L D, Laing W, Ferguson L R, Skinner M A (2009). Kiwifruit-based polyphenols and related antioxidants for functional foods: kiwifruit extract-enhanced gluten-free bread. Int J Food Sci Nutr. 60 Suppl 7:251-64. Epub
5. Daigo Abe, Takeshi Saito, Yasutaka Kubo, Yoshimasa Nakamura, Keizo Sekiya A fraction of unripe kiwi fruit extract regulates adipocyte differentiation and function in 3T3-1.1 cells, Biofactor vol.
6. Duttaroy, A K, and Jorgensen A. J. (2004) Effects of kiwi fruit consumption on platelet
   aggregation and plasma lipids in healthy human volunteers. Platelets 15, 287-292 13(2):67-75

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of this invention are intended to be within the scope of the following claims.

The invention claimed is:

1. An oral delivery vehicle comprising an effective amount of a water-soluble fraction obtained from *Actinidia deliciosa*,
    wherein said fraction consists essentially of molecules having a molecular weight of less than 1000 daltons,
    wherein said oral delivery vehicle is selected from the group consisting of a tablet, capsule, pill, and dragee; and
    wherein said fraction is prepared by:
        (a) filtering an aqueous *Actinidia deliciosa* extract through an ultrafilter having a molecular weight cutoff of 1000 Daltons; and
        (b) collecting the filtrate to obtain said water-soluble fraction.

* * * * *